United States Patent [19]

Lee

[11] 4,167,181
[45] Sep. 11, 1979

[54] APPARATUS FOR AUTOMATICALLY DEPRESSURIZING A VARIABLE-VOLUME INFLATABLE ENCLOSURE

[75] Inventor: Arnold S. J. Lee, Englewood, N.J.

[73] Assignee: Milstein Medical Research Foundation, Inc., New York, N.Y.

[21] Appl. No.: 778,995

[22] Filed: Mar. 18, 1977

Related U.S. Application Data

[60] Division of Ser. No. 617,175, Sep. 26, 1975, Pat. No. 4,027,662, which is a continuation of Ser. No. 378,167, Jul. 11, 1973, abandoned.

[51] Int. Cl.² ............................................. A61B 5/02
[52] U.S. Cl. .................................... 128/682; 137/102
[58] Field of Search ............... 128/2.05 A, 2.05 G, 128/2.05 M, 2.05 D; 137/102, 115; 128/145.6

[56] References Cited

U.S. PATENT DOCUMENTS

| | | | |
|---|---|---|---|
| 2,292,302 | 7/1961 | Schuler | 137/102 |
| 3,033,195 | 5/1962 | Gilroy et al. | 128/DIG. 17 X |
| 3,104,661 | 9/1963 | Halpern | 128/2.05 A |
| 3,485,238 | 12/1969 | Kostrov et al. | 128/2.05 G |
| 3,552,383 | 1/1971 | Krueger | 128/2.05 A |
| 3,730,172 | 5/1973 | Buddecke et al. | 128/2.05 M |
| 3,905,353 | 9/1975 | Lichowsky | 128/2.05 M X |
| 4,116,230 | 9/1978 | Gorelick | 128/2.05 M |

Primary Examiner—Robert W. Michell
Assistant Examiner—Francis J. Jaworski

[57] ABSTRACT

A pneumatic regulator including a constant-volume reference chamber and associated pressure-sensitive inflation and deflation valves is provided to effect a precise linear depressurization of a variable-volume inflatable enclosure, such as a cuff which has been applied to a patient during a blood pressure measurement thereof and pressurized to a value higher than the patient's systolic pressure. By coupling such regulator to the drive for one axis of an X-Y recording chart, the pen or marker of the chart can be precisely scanned along the associated chart axis at the constant depressurization rate of the cuff.

3 Claims, 2 Drawing Figures

APPARATUS FOR AUTOMATICALLY DEPRESSURIZING A VARIABLE-VOLUME INFLATABLE ENCLOSURE

This is a division of application Ser. No. 617,175, filed Sept. 26, 1975 now U.S. Pat. No. 4,027,662, said application being a continuation of Ser. No. 378,167 filed July 11, 1973 and now abandoned.

BACKGROUND OF THE INVENTION

The invention relates to apparatus for automatically depressurizing a variable-volume inflatable enclosure, such as a cuff.

In the past a number of inventors have sought to provide machines that automatically detect blood pressure and automatically indicate and/or record the detected measurements on an X-Y chart or the like in such manner that a physician or other trained observer can rapidly determine the systolic and diastolic pressures at a glance from the recording and can easily distinguish the valid pressure markings from artifacts.

Typically, the blood pressure measurements are taken with the aid of an inflatable cuff which has been applied to a patient and pressurized to a value initially higher than the patient's systolic pressure and which has thereafter been depressurized. The scan of the timing axis of the X-Y chart is syncchronized with the rate of depressurization of the cuff.

One problem with such arrangements is that the linearity of the depressurization, and thereafter the accuracy of the scan of the chart drive, has not been sufficiently precise to obtain an optimum display and/or record for the observer.

SUMMARY OF THE INVENTION

To solve this problem, the invention provides an improved apparatus for automatically depressurizing a variable-volume inflatable enclosure, such as a cuff, at a precisely constant rate.

In an illustrative embodiment, the arrangement includes a reference chamber having a fixed volume, which is pressurized to a value at least as high as the starting pressure for depressurization. During the pressurizing of the reference chamber, the inflatable enclosure is simultaneously pressurized to such starting rate of pressure. When the pressure in the reference chamber has reached the desired value, the chamber is depressurized through a vent valve coupled to the inflatable enclosure. A control element simultaneously coupled to the chamber, the source of pressure for the enclosure and the chamber, and the vent valve maintains a predetermined difference in pressure between the reference chamber and the enclosure to maintain the desired precisely linear depressurization of the enclosure.

DESCRIPTION OF A PREFERRED EMBODIMENT

Very generally according to one embodiment of the invention, an adjustable automatic timer periodically initiates the rapid inflation and relatively slow deflation of a flexible cuff encircling the arm of a patient over the range of pressures exceeding systolic to below diastolic pressure, and during each deflation portion of the cycle a series of blood flow surges are detected to generate electrical signals in response to each opening of the artery from a collapsed condition. As is well known, the arterial system of the body and surrounding tissue are substantially elastic and the external pressure cuff serves to collapse the artery whenever external pressure in the cuff exceeds internal arterial pressure, and alternatively, the artery walls decollapse or open when the internal pressure exceeds the external, resulting in a blood flow surge. The series of electrical signals are electrically processed to minimize artifacts and the processed signals are then applied to modulate a pen or suitable marker in such fashion as to graphically record a single valued function, with the individual markings on the record providing an adjustable indication of the "strength" of the blood flow surges and the position of such markings across the record indicating both the externally applied pressure in the cuff at the time of the surge and the time of the surge during the deflation cycle. The plural markings for each measurement are recorded along a line transversely across a slowly moving record. Along the length of the record in the direction of its movement the record is printed with the time of day to show the time at which each measurement is made. The record is also printed in a direction transverse to its direction of movement according to pressure graduations so that the location of the markings show the cuff pressure. The record is preferably continuously driven during the automatic operation of the machine so that for each succeeding measurement, the record has been advanced to enable the series of processed signals corresponding to surges to be recorded in a line disposed in parallel relationship to the line of markings for the preceeding measurement. Since for each measurement, each marking along the line corresponds to a different cuff pressure, the first marking for each measurement indicates the systolic pressure and the last marking indicates diastolic pressure.

Figure 1:
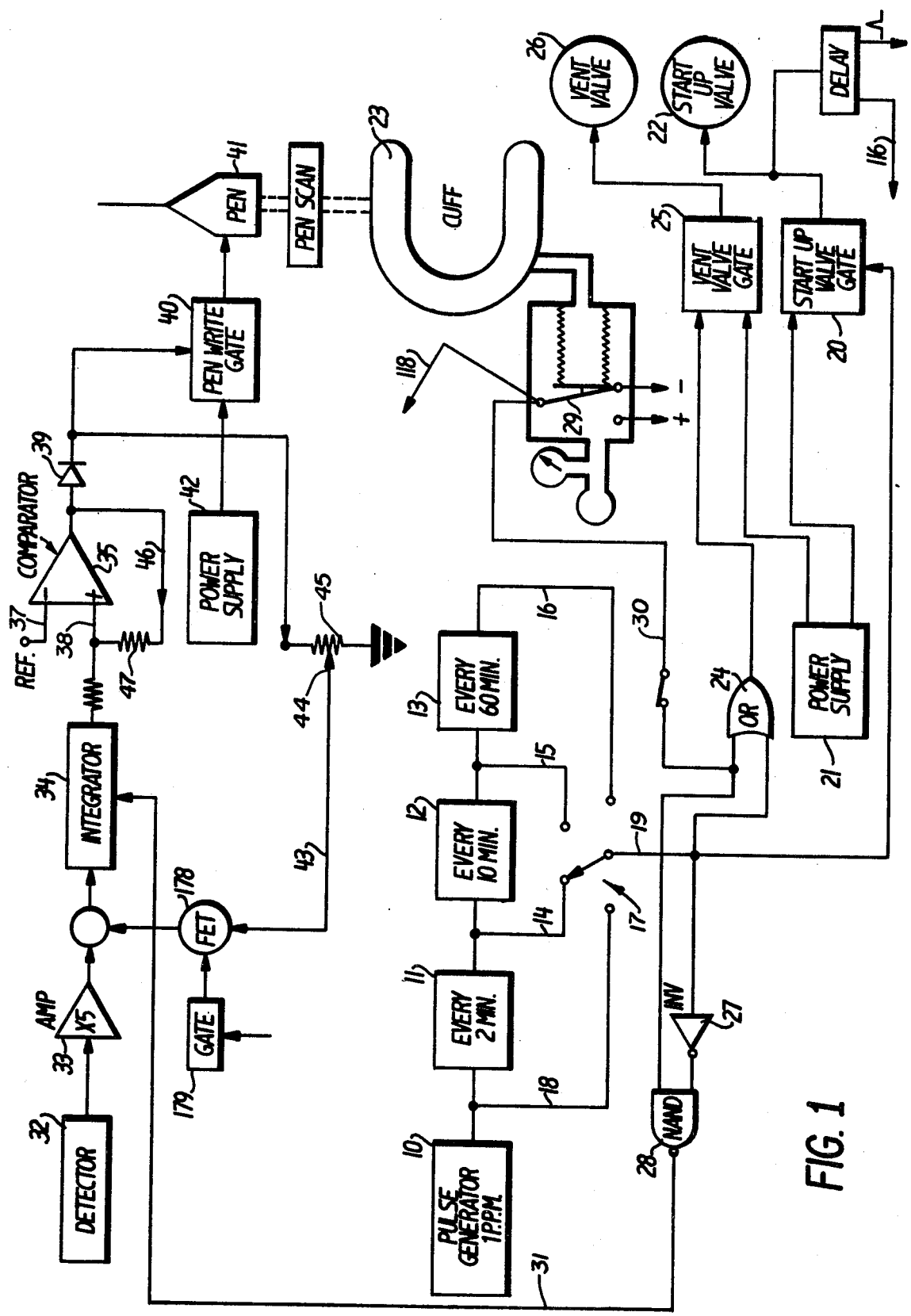
FIG. 1 is an electrical schematic diagram illustrating a preferred embodiment for recording only a single valued function.

With this general introduction, reference is now made to FIG. 1, showing an electrical system for a preferred embodiment.

As shown, an automatic timer mechanism comprises an electronic oscillator 10 producing uniform pulses of four second duration and at a slow frequency of one such pulse every minute. These oscillator pulses are directed to three frequency dividers 11, 12, 13 disposed in cascaded relationship providing successive frequency division of scale of two, scale of 5, and scale of 6, respectively. Accordingly, the output of 14 of divider 11 produces one such pulse every two minutes; divider 12 produces an output pulse over line 15 every ten minutes; and divider 13 produces an output pulse over line 16 every sixty minutes. A manually adjustable multiposition switch 17 is provided with terminals connected to all output lines 18, 14, 15, and 16, and accordingly the switch 17 is adjustable to select repetition of the machine every minute, every two minutes, every ten minutes, or every sixty minutes, as might be desired.

These timer generated pulses are directed over line 19 to initiate operation of both the pneumatic system for inflating the cuff, and the detecting and recording system for recording the measurements.

For initiating the pneumatic cuff inflation mechanism, the timer pulse from selector switch 17 is directed over line 19 to a start-up valve gate 20, thereby opening the gate 20 to energize a solenoid operated start-up valve 22 which is powered by a power supply 21. The start-up valve 22 is thereby opened for the four second interval of the timer pulse to apply air pressure from a pressurized source to inflate the cuff 23. Concurrently, the timer pulse over line 19 is also passed through "or" circuit 24 to energize a vent valve gate 25, thereby closing a normally open solenoid vent valve 26. As will be seen, this prevents venting of the pressurizing system during inflation of the cuff 23.

The timer pulse over line 19 is also directed to an inverter circuit 27 and to a "Nand" circuit 28 to ready or condition the electrical detecting and measuring system for operation.

As the cuff 23 is inflated to beyond a preset "dump" pressure, a bellows operated switch 29 responsive to cuff pressure is closed to apply a voltage of the correct polarity over line 30 to the second input of "Nand" circuit 28, whereby the "Nand" circuit is thereupon properly energized to produce a reset pulse over 31 to the integrator in the electrical system for conditioning the electrical system to commence a new operation.

The signal over line 30 from bellows switch 29 is also passed through "or" circuit 24 to the vent valve gate 25, thereby maintaining the solenoid operated vent valve 26 in a closed condition and preventing venting of the pneumatic system during this portion of the cycle of blood pressure measurement.

Upon the cuff 23 being inflated to a preset pressure above systolic during the four second interval, it immediately commences to depressurize in a precisely controlled linear manner, as will be described; and during such linear depressurization portion of the cycle, a suitable detector 32 detects a series of blood flow surges that occur as the cuff pressure is progressively diminished between systolic and diastolic pressure.

For example, the cuff pressure is initially rapidly inflated to some preset pressure over systolic, such as above 150 Torr, and the cuff is then depressurized in a linear manner at a rate of about 6 Torr every second to a "dump" pressure below diastolic; over a time interval of about 30 seconds. As the cuff pressure diminishes toward the patient's systolic pressure, the arteries are periodically collapsed and then opened following each heart beat, thereby producing a blood flow surge during each opening, and such surges are detected by detector 32 to produce an electrical burst signal for each such surge.

In a preferred embodiment, the detector employed is of the doppler ultrasonic type, such as is disclosed in Ware U.S. Pat. No. 3,527,197, that produces an electrical burst signal proportional to the rate-of-movement of the arterial wall. However, it will be appreciated by those skilled in the art that other detectors, including microphones, may be employed for this purpose to detect the surges as disclosed in Applicant's earlier application.

These low level blood flow surge signal bursts are amplified by a factor of about 5 by an amplifier 33, and then rectified; and the rectified and amplified negative polarity bursts are then suitably processed by an "interposition" circuit to minimize the transmission of artifacts and meaningfully energize the recorder. As will be seen, the purpose of the "interposition" circuit is to assist in minimizing the recording of spurious signals and to obtain quantized pulses for recording that are representative of the "strength" of the blood flow surges. Since the preferred doppler type ultrasonic detector 32 produces burst signals proportional to the rate-of-movement of the arterial wall, a preferred "interposition" circuit operates to integrate these bursts, and to provide pulses of variable duration in proportion to the "size" of the bursts, including their amplitude and duration. It will be understood, however, by those skilled in the art that these bursts may be processed according to other mathematical functions to derive useful signals for recording that will indicate to the physician the "strength" of the blood flow surge through the artery.

Returning to FIG. 1, each of the amplified and rectified burst signals is applied as a negative polarity signal to an integrator 34 to rapidly raise the output of integrator 34 to a dc level according to the combined amplitude and duration of its input, and to retain the output at this dc level. This integrated signal is then directed to a comparator circuit 35 characterized by producing either a negative or positive dc output at constant amplitude of about 12 volts depending upon the values of the combination of input voltages on its dual inputs 37 and 38. The output of comparator 35 is normally at negative voltage due to a reference voltage applied at input 37; and a diode 39 in the output circuit prevents the further transmission of this constant negative voltage. However, upon the output of integrator 34 rising above a preset level, the output of the comparator 35 is promptly "jumped" to its positive voltage level which is transmitted through diode 39 to energize the pen gate circuit 40 controlling the marking by the pen 41 or other recording marker that is powered by power supply 42. So long as the output of comparator 35 is positive, the pen 41 or marker is continuously energized by its power supply 42 to provide a continuous marking.

However, as will be recalled in this embodiment it is desired to graphically record dashes of adjustable length proportional to the "strength" of the detected surges. This is performed by feeding back a low level constant positive dc voltage from the output of comparator 35 over line 43 to the input of integrator 34 in opposition to the original negative voltage from the detector circuit. This constant dc feedback is obtained via a potentiometer 44 and a series resistor 45 that are coupled to the output of diode 39. As previously noted, the voltage over line 43 is positive and in opposition to the negative going detector signals, and is also at a much lower level than such signals whereby this constant feedback signal is progressively integrated by integrator 34 and operates to slowly lower or diminish the output of integrator 34 from the output level that it reached when driven by the previously received negative signal from the detector circuit. After a period of time related to the level of the previously integrated detector signal, the output of integrator 34 is progressively diminished to below the level of the reference voltage applied to comparator 35, and the comparator output is accordingly flipped backwardly or returned from its constant positive voltage output to its original constant negative level. This negative output is not transmitted through diode 39, and the energizing signal applied to the pen gate 40 controlling the marking by pen 41 is accordingly terminated, thereby to terminate the marking by the pen 41 in response to that detected blood pressure surge. In short, the integrator 34 provides a variable amplitude output corresponding to the detected surge signal and the combination of integrator and comparator convert this to a pulse of adjustable width or time duration.

Briefly recapitulating the functioning of the detector circuit and interposition circuit, each blood flow surge occuring when the cuff pressure is between systolic and diastolic pressure is detected by the ultrasonic doppler detector 32 to produce a low level signal burst characterized by representing the rate-of-movement of the artery during movement from a collapsed to an open condition. This low level burst signal is amplified to a useful level and rectified, and then applied to a store and hold integrator 34, having a variable output amplitude corresponding to the content of the detector burst. This jump in integrator output drives the output of a comparator 35 from a constant negative voltage to a constant positive voltage, thereby energizing the pen 41 to commence writing. A constant low level positive signal is also directed backwardly to the integrator to progressively diminish the output of integrator 34 from the level of the "stored" detector burst, and thereby after a variable time duration that is proportional to the amplitude of the integrated burst signal, the comparator 35 is flipped backwardly to its constant negative voltage to terminate the marking or recording by the pen 41.

To prevent a spurious artifact signal from inadvertantly triggering the operation of the comparator 35, the comparator circuit is provided with positive feedback from its output to input, via line 46 and summing resistor 47. The effect of this feedback is to require a greater positive polarity signal than the reference signal on line 37, to initially trigger the comparator 35 to jump from its negative to positive output and start the writing of the pen; and conversely to require that the integrator output be driven below the reference voltage on line 37 in order to terminate the writing of the pen. This is performed as follows: before writing of the pen 41, the output of comparator 35 is at constant negative polarity, and a small portion of this negative signal is fed back to the input over feedback loop 46. To trigger the comparator 35, the output of integrator 34 must then exceed the sum of the reference voltage on line 37 and the level of dc feedback over line 46. Conversely, after the comparator 35 has been triggered and its output is at positive polarity, the dc feedback is in a direction or polarity opposing that of the reference on line 37, thereby diminishing the net reference voltage applied to the comparator 35. Consequently the output of integrator 34 must then be diminished to a level below the difference between reference voltage and feedback on 46 in order to trigger the comparator 35 backwardly to its initial negative output condition.

Pneumatic System

According to a preferred embodiment, it is desired that during each measurement, the depressurizing or bleed of air from the cuff be regulated in a precisely linear fashion and that the scanning or positioning of the pen or marker across the record be controlled by existing pressure in the cuff. In this manner during each measurement the recording marker is scanned across the record in a precisely linear fashion and the beginning location of each of the markings on the record corresponds to the time during the cycle when that blood flow surge is detected and also corresponds to the cuff pressure for that surge. As will be seen, this linear depressurization enables artifactual signals to be more readily distinguished from valid blood flow surges and also enables the recording to more readily indicate arrythmias in the heartbeat.

Since the inflatable cuff 23 is an elastic member whose volume changes with the degree of deflation, in order to obtain a linear or uniform decline in pressure in the cuff over the deflation portion of the cycle, it is necessary that the air be evacuated from the cuff in a nonlinear manner. According to the present invention, this controlled nonlinear bleed in the cuff is obtained by employing a constant volume reference container having rigid walls, and by linearly pressurizing and depressurizing the reference container with air to in turn regulate the linear pressurizing and depressuring of the flexible cuff. Since the reference container has a constant volume it may be precisely linearly depressurized by a constant flow evacuation of air therefrom.

Figure 2:
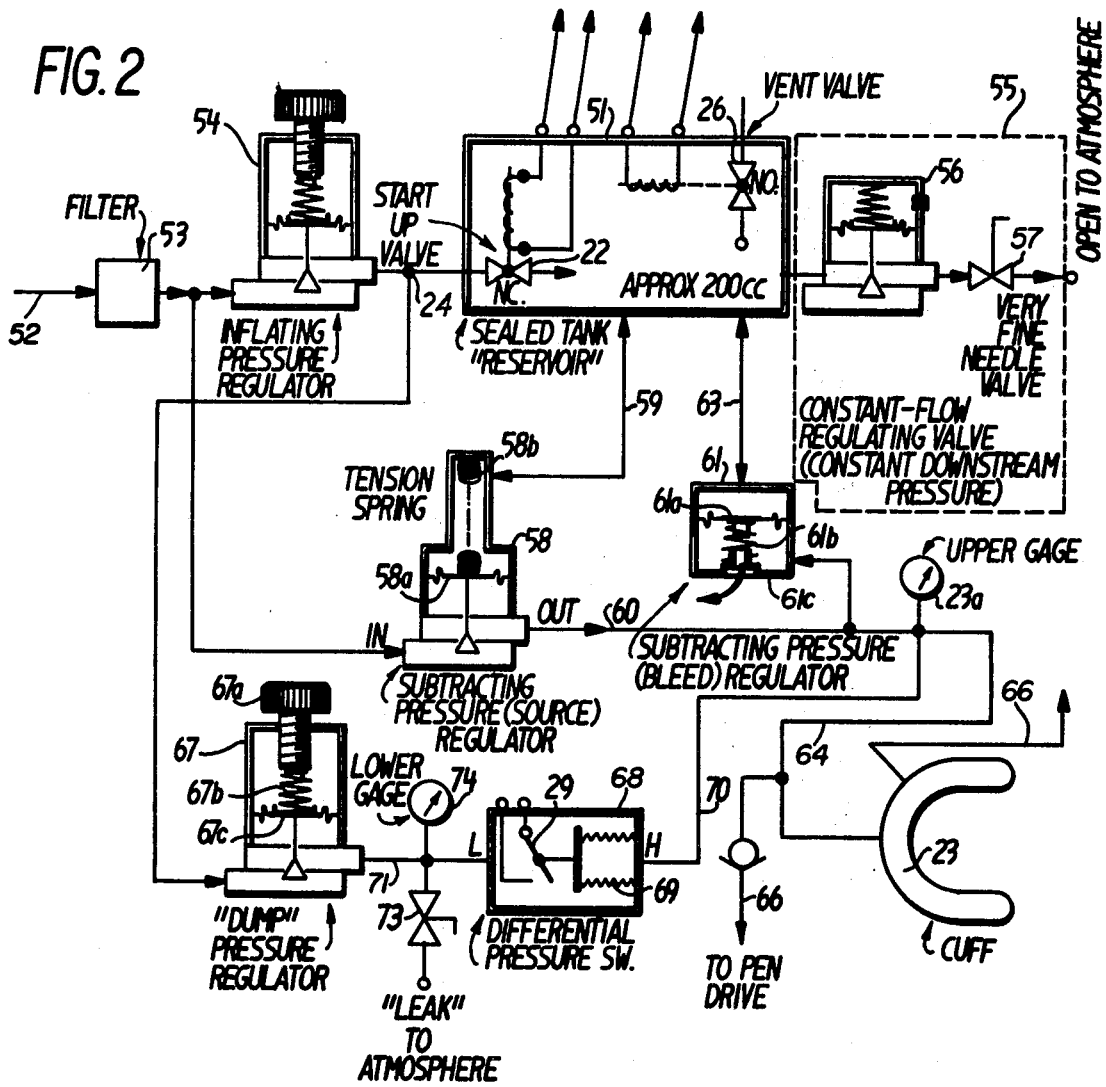
FIG. 2 is a schematic illustration depicting a preferred pneumatic system for providing a regulated precise linear depressurization of the cuff.

Referring to FIG. 2, for a detailed consideration of a preferred linearizing pneumatic system, a constant volume reference tank 51 is provided with a normally closed solenoid operated start-up valve 22 at the inlet 24 and a normally open solenoid operated vent valve 26 at an outlet. Upon the start-up pulse from the timer energizing the start-up valve gate 20 and energizing the vent valve gate 25, as described above, pressurized gas from a source (not shown) is directed over an inlet line 52 and through a suitable filter 53 to an adjustable inflating pressure regulator valve 54. During a short portion of the four second interval when the start-up valve 22 is opened in response to the timer pulse, the reference tank 51 is pressurized by the inlet gas to a pressure that is preset by the inflating pressure regulator valve 54, whereupon the regulator valve 54 automatically closes. This regulator valve 54 is preset to a pressure that is 5 PSI above the desired maximum pressure desired in the cuff 23.

At the outlet of the constant volume reference tank 51 is provided a constant flow regulating valve mechanism 55 that provides a regulated constant flow of gas and accordingly a linear depressurization of air from the tank 51. This constant flow mechanism comprises a pressure regulating valve 56 disposed in series with a very fine needle valve 57 whose outlet is open to the atmosphere. The regulating valve 56 is adjusted to regulate the gas pressure at the inlet of the needle valve 57 to a constant pressure of about 5 PSI above atmospheric pressure. Therefore with a constant pressure across the needle valve 57, the needle valve passes or bleeds a constant flow of air from the reference tank 51 to the atmosphere. Since the reference tank 51 encompasses fixed volume enclosure, this constant flow of air from the tank provides a regulated linear decline in pressure in the tank 51.

For pressurizing and depressurizing the flexible cuff 23, the pressurized inlet source after the inlet filter 53, is also directed to a subtracting pressure regulator valve 58 for regulating the pressure to the cuff 23 from the source. Valve 58 is of the differentially operated type having two chambers separated by a flexible diaphram 58a for operating the valve. The upper chamber is coupled to and senses the reference pressure in the tank 51 over line 59 and the lower chamber is coupled to and senses the pressure in the cuff over line 60. A tension spring 58b provides an upward pull on the diaphram 58a of about 5 PSI to maintain this valve normally closed.

Upon pressurizing the tank 51, the cuff 23 is therefore rapidly inflated to a pressure of 5 PSI less than the pressure in the tank 51 through the action of the subtracting pressure regulator valve 58 that is opened to admit pressurized gas into the cuff 23 whenever the cuff pressure is more than 5 PSI less than that of the reference tank 51. For depressuring the cuff 23 whenever its pressure is greater than within the 5 PSI of the reference tank 51, a second subtracting pressure regulator valve 61 is employed to compare and regulate the pressure in the cuff 23 to that in the reference tank 51. This second subtracting regulator valve 61 senses the pressure in the reference tank 51 via line 63, and that in the cuff 23 over line 64, and functions to bleed the cuff pressure to atmosphere whenever its outlet 61c rises to greater than 5 PSI of the pressure in reference tank 51. As generally shown, this valve 61 is also divided into upper and lower chambers by a flexible diaphram 61a, and is biased by a spring 61b. Any excess of pressure in the cuff 23 over that in the tank 51 as modified by the spring operates on the diaphram to open the valve 61 and bleed the air from the cuff 23 to atmosphere until the preset differential pressure is reached, whereupon valve 61 is again closed to stop the leakage of air from the cuff 23. Thus subtracting regulator valve 58 constantly regulates the admission of pressurized gas into the cuff 23 whenever the reference tank 51 pressure is above that preset for the cuff 23, and the second subtracting regulator valve 61 exhausts compressed air from the cuff 23 to atmosphere whenever the opposite condition prevails; the combination of these two valves 58 and 61 therefore constantly regulates the pressure in the cuff 23 both upwardly and downwardly to closely follow that of the reference tank 51.

As will be recalled, the pressure in the reference tank 51 is progressively reduced at a precisely linear regulated rate by the action of the constant flow regulating valve mechanism 55. Consequently the pressure in the cuff 23 is likewise lessened at a precisely linear regulated rate by the action of the two subtracting regulating valves 58 and 61. Thus for each blood pressure measurement, the tank 51 is automatically inflated to 5 PSI above a desired pressure for the cuff and is progressively deflated or depressurized at a precisely controlled linear rate by the reference tank 51 and valve mechanism as described. As will be seen, the regulated pressure in the cuff 23 is also directed over line 66 to control the scanning movement of the pen 41 or marker so that during the depressurization portion of the measurement cycle when the blood flow surges are being detected, the pen 41 or marker is also scanning across the record at a precisely controlled linear rate.

After the cuff has completed its linear rate of depressurization to a pressure below diastolic pressure, it is desired that the cuff pressure then be rapidly emptied or "dumped" to atmospheric pressure. The reason for this action is to promptly remove any external pressure from the limb after the measurement has completed so as not to interfere with the blood return circulation through the veins which occurs at a much lower pressure than diastolic pressure in the arteries. To perform this function, there is provided an adjustable "dump" pressure regulator valve 67 and a differential pressure operated switch 68. The "dump" pressure regulator valve 67 is similar to the adjustable inflating regulator valve 54 and is provided with a manually turnable screw 67a for adjusting the compression of bias spring 67b that operates on a diaphram 67c for opening and closing the valve mechanism. This regulator valve 67 senses and regulates a fixed present pressure reference on line 71 leading to an inlet of differential pressure switch 68. The other inlet to differential pressure switch 68 is over line 70 from the cuff pressure leading to an expandable bellows 69 inside the switch housing 68. So long as the pressure in the cuff 23 is above the low "dump" reference pressure on line 71 (preset by regulator valve 67) the bellows 68 is expanded to a position keeping electrical contacts 29 closed. As described in FIG. 1, these contacts apply energization through gate 25 to the solenoid of the vent valve 26 located at an outlet from the reference tank 51, and this energized solenoid valve 26 is kept closed to prevent venting of the reference tank 51. However, upon the cuff pressure dropping below diastolic to the preset "dump" level on line 71, the bellows 69 is compressed to open the electrical contacts 29 and deenergize the vent valve gate 25. Since the vent valve 26 is a normally open valve, the deenergization of its solenoid results in opening of this valve to evacuate or "dump" the remaining pressure in the reference tank 51 to the atmosphere. The subtracting pressure regulator valve 61 correspondingly senses the drop to atmospheric pressure of tank 51 and correspondingly vents the cuff 23 to its atmosphere. For proper functioning of the "dump" regulator valve 67, a very small needle valve leak 73 to atmosphere is provided in line 71 and a pressure gage 74 is provided in this line to indicate the preset level of the "dump" pressure.

I claim:

1. Apparatus for automatically depressurizing a variable-volume inflatable enclosure such as a cuff at a precisely constant rate, the apparatus comprising, in combination, a reference chamber having a fixed volume, means for pressurizing the reference chamber to a fixed value, means operable for pressurizing a variable-volume inflatable enclosure, means operative when the reference chamber has reached the fixed value for depressurizing the reference chamber at a precisely constant rate, vent valve means coupled to the enclosure and operable for depressurizing the enclosure, and control means coupled to the reference chamber, the enclosure pressurizing means and the vent valve means for selectively operating the enclosure pressurizing means and the vent valve means to maintain a predetermined difference in pressure between the reference chamber and the enclosure as the reference chamber is depressurized at the precisely constant rate.

2. Apparatus for automatically depressurizing a variable-volume inflatable enclosure such as a cuff at a precisely constant rate from a first value, the apparatus comprising, in combination, a reference chamber having a fixed volume, means for pressurizing the reference chamber to a second value higher than the first value, means operable for pressurizing a variable-volume inflatable enclosure, means operative when the reference chamber has reached the second value for depressurizing the reference chamber at a precisely constant rate, vent valve means coupled to the enclosure and operable for depressurizing the enclosure, and control means coupled to the reference chamber, the enclosure pressurizing means and the vent valve means for selectively operating the enclosure pressurizing means and the vent valve means to maintain the pressure in the enclosure a predetermined amount below the pressure in the reference chamber as the reference chamber is depressurized at the precisely constant rate.

3. Apparatus for automatically depressurizing a variable-volume inflatable enclosure such as a cuff at a constant rate, the apparatus comprising, in combination, a reference chamber having a fixed volume, means for pressurizing the reference chamber to a fixed value, means operable for pressurizing a variable-volume inflatable enclosure, means operative when the reference chamber has reached the fixed value for depressurizing the reference chamber at a precisely constant rate, means operable for depressurizing the enclosure, first means for operating the enclosure pressurizing means when the pressure in the enclosure is lower than a predetermined amount below that of the reference chamber, and second means for operating the enclosure depressurizing means when the pressure in the enclosure is greater than a predetermined amount below that of the reference chamber.

* * * * *